(12) United States Patent
McInnes et al.

(10) Patent No.: US 9,456,990 B2
(45) Date of Patent: Oct. 4, 2016

(54) MULTI-COMPARTMENTED CONTAINER

(71) Applicant: Capsugel Belgium NV, Bornem (BE)

(72) Inventors: Clinton Wesley McInnes, Greenwood, SC (US); Anna Marie Underwood, Greenwood, SC (US); Phillip Andrew Vickery, Greenwood, SC (US)

(73) Assignee: Capsugel Belgium NV, Bornem (BE)

( * ) Notice: Subject to any disclaimer, the term of this patent is extended or adjusted under 35 U.S.C. 154(b) by 0 days.

(21) Appl. No.: 14/602,929

(22) Filed: Jan. 22, 2015

(65) Prior Publication Data

US 2015/0132376 A1 May 14, 2015

Related U.S. Application Data

(62) Division of application No. 12/682,962, filed as application No. PCT/IB2008/054220 on Oct. 14, 2008, now Pat. No. 8,968,717.

(60) Provisional application No. 60/981,147, filed on Oct. 19, 2007.

(51) Int. Cl.
*A61K 9/48* (2006.01)
*A61J 3/07* (2006.01)

(52) U.S. Cl.
CPC ............ *A61K 9/4808* (2013.01); *A61J 3/071* (2013.01)

(58) Field of Classification Search
None
See application file for complete search history.

(56) References Cited

U.S. PATENT DOCUMENTS

| 4,487,327 A | * | 12/1984 | Grayson .................... 220/8 |
| 4,893,721 A | | 1/1990 | Bodenmann et al. |
| 5,750,143 A | * | 5/1998 | Rashid et al. ............. 424/451 |
| 5,756,123 A | | 5/1998 | Yamamoto et al. |
| 5,769,267 A | | 6/1998 | Duynslager et al. |
| 2007/0036830 A1 | | 2/2007 | Vanquickenborne et al. |
| 2007/0087048 A1 | * | 4/2007 | Abrams et al. ............ 424/451 |
| 2008/0160076 A1 | | 7/2008 | Hochrainer et al. |
| 2009/0232886 A1 | | 9/2009 | Sison |

FOREIGN PATENT DOCUMENTS

| DE | 1281633 | 10/1968 |
| DE | 19835346 | 2/2000 |
| JP | H05-271055 | 10/1993 |
| JP | H06-505263 | 6/1994 |
| JP | 2003-505498 | 2/2003 |
| TW | 1221420 | 10/2004 |
| WO | WO 92/13521 | 8/1992 |
| WO | WO 01/08666 | 2/2001 |
| WO | WO 2005/039474 | 5/2005 |
| WO | WO 2007/017725 | 2/2007 |
| WO | WO 2007/047371 | 4/2007 |

OTHER PUBLICATIONS

International Search Report for related International Application No. PCT/IB2008/054220, mailed Jun. 5, 2009.

(Continued)

*Primary Examiner* — Brian Gulledge
(74) *Attorney, Agent, or Firm* — Klarquist Sparkman, LLP

(57) ABSTRACT

The invention provides a multi-compartmented container suitable for the delivery of pharmaceuticals, medicines, vitamins, and the like.

11 Claims, 5 Drawing Sheets

(56) References Cited

OTHER PUBLICATIONS

Notice of Allowance from the United States Patent & Trademark Office in co-pending U.S. Appl. No. 12/682,962, dated Oct. 27, 2014.
Office Action from the United States Patent & Trademark Office in co-pending U.S. Appl. No. 12/682,962, dated Jul. 19, 2012.
Final Office Action from the United States Patent & Trademark Office in co-pending U.S. Appl. No. 12/682,962, dated Jan. 4, 2013.
Final Office Action from the United States Patent & Trademark Office in co-pending U.S. Appl. No. 12/682,962, dated May 1, 2013.
Office Action from the United States Patent & Trademark Office in co-pending U.S. Appl. No. 12/682,962, dated Jul. 2, 2014.

* cited by examiner

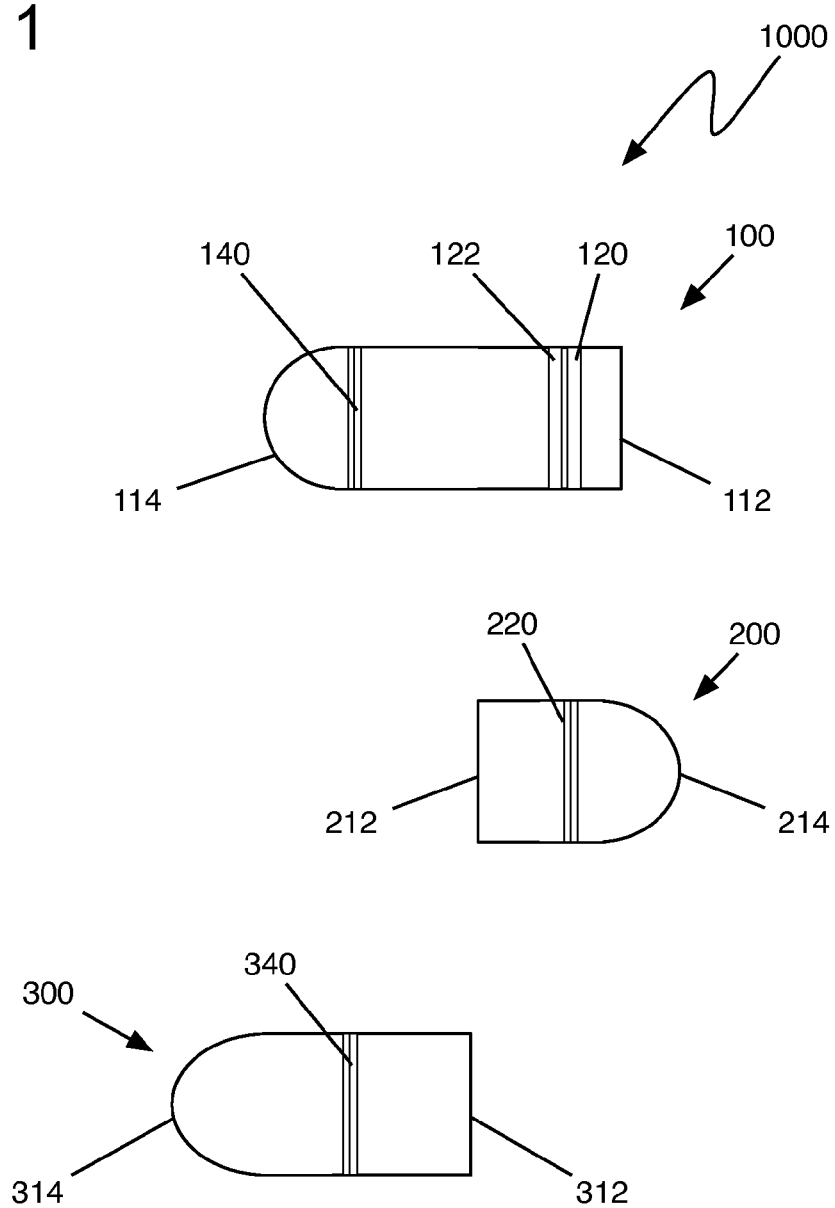

MULTI-COMPARTMENTED CONTAINER

CROSS REFERENCE TO RELATED APPLICATIONS

This is a Divisional of U.S. patent application Ser. No. 12/682,962, filed Apr. 14, 2010, which is the U.S. National Stage of International Application No. PCT/IB2008/054220, filed Oct. 14, 2008, which in turn claims the benefit of U.S. Provisional Application No. 60/981,147, filed Oct. 19, 2007, all of which are hereby incorporated by reference in their entirety.

FIELD OF THE INVENTION

The invention relates generally to containers, and more particularly, to multi-compartmented containers, such as capsules for the delivery of pharmaceuticals, medicines, vitamins, and the like.

BACKGROUND OF THE INVENTION

Capsule technology continues to be subject to development and improvements. In its basic form, standard containers for pharmaceuticals or other powdered, granular, or liquid substances, so-called telescope-type capsules, include a tubular-shaped or cylindrically-shaped first part, namely the cap part, which is closed on one end and open on the other end. A tightly fitting second part of similar shape, but of smaller diameter, can be telescopically inserted into the cap part, the second part being referred to as the main part or body part.

Separation of the cap and body is often prevented by friction and/or various modifications of an exterior surface of the body and/or an opposed inner surface of the cap. Usually, the containers are supplied to a filling apparatus in a "prelock" (or pre-closed) condition in which the body part is telescoped only partially into the cap. The two parts are separated in the filling machine and then fully closed after the filling operation.

In addition to various locking mechanisms intended to secure the various parts of a multi-part capsule after filling, the parts may alternatively or additionally be sealed by various methods. Generally, such sealing includes the spraying with a liquid or dipping of the capsule parts in a liquid. Such liquid may itself provide adhesive and/or sealing properties. Alternatively, such liquid may result in the partial dissolution or disintegration of portions of the capsule parts, whereby the capsule parts are fused or sealed upon evaporation of the liquid. Illustrative liquid sealing methods and solutions are disclosed in U.S. Pat. No. 4,893,721 to Bodenmann et al., which is hereby incorporated by reference.

U.S. patent application Ser. No. 11/485,686, US 2007-0036830A1 to Vanquickenborne et al., which is also incorporated by reference, describes a capsule having a pre-lock position and a lock position, and a fluid gap between the cap and body that aids in restricting a sealing fluid between the cap and body, thereby improving the seal between the cap and body. The particular sealing fluid chosen will depend, in part, upon the composition of the capsule parts, but may include, for example, water or an alcohol. Capsules may be constructed from a variety of film-forming agents such as gelatin, hydroxypropylmethylcellulose (HPMC), pullulan, etc.

U.S. Pat. No. 5,769,267 to Duynslager et al., also incorporated by reference with regard to the structure of the capsule products disclosed, describes a particular type of telescoping capsule with pre-lock and lock positions.

Commercial products include those sold under the names Coni-Snap® and Qualicaps.

Once filled and closed, containers such as those described above comprise a single interior volume within which their contents are enclosed and from which their contents are ultimately delivered. However, many pharmaceuticals, vitamins, and the like are more effective when delivered in more than one dose or when delivered in combination with another compound. Thus, in order to provide such multiple or combination doses, the compounds themselves are typically modified to provide sustained, pulsatile, or delayed release. This can be an expensive process and requires specialized equipment.

Thus, it would be advantageous to have a container which had separate compartments and which provided the ability to deliver multiple ingredients wherein the ingredients were kept separate until dosing. It is a further benefit of the invention to provide such a container with separate compartments so that ingredients that were incompatible (especially during storage and before dosing) or which reacted in contact with each other could be in the form of a single container. It is yet another goal of the present invention to provide a container with the ability to create a unique and attractive appearance for marketing, to obtain improved compliance in dosing (for example, in pediatric use). To this extent, a need exists for containers, such as pharmaceutical capsules, that permit multiple or combination doses to be administered to an individual that, for example, do not require the delivered compound(s) to be modified (such as the formation of salts or derivatives of the compound) to provide such multiple or combination doses which otherwise would normally require separate delivery vehicles.

SUMMARY OF THE INVENTION

The invention provides a multi-compartmented hard shelled container suitable for the delivery of pharmaceuticals, medicines, vitamins, minerals, dietary supplements, homoeopathic ingredients, and combinations of the foregoing, and the like.

A first aspect of the invention provides a container including
a hard shell capsule comprising a body and a cap telescopically fitted on the body in a common axial direction, said capsule defining a first compartment for accommodating a first dose of a compound;
a capping member attached to the capsule and defining therebetween a second compartment for accommodating a second dose of a compound in a separate manner from the first dose,
wherein the capping member is a hard shell telescopically and coaxially fitted on the capsule.

A second aspect of the invention provides a container comprising: a top cap having an open end, a closed end, and at least one inwardly-projecting annular ridge; a bottom cap having an open end, a closed end, and at least one inwardly-projecting annular ridge; and a body having an open end, a closed end, and an outer surface having at least three annular grooves, wherein the open end of the body is adapted to slide inside the open end of the top cap such that the at least one inwardly-projecting annular ridge of the top cap is alternately engagable with at least two of the at least three annular grooves, and wherein the closed end of the body is adapted to slide inside the open end of the bottom cap such that the at least one inwardly-projecting annular ridge of the bottom cap is engagable with at least one of the at least three annular grooves.

A third aspect of the invention provides a pharmaceutical dosage form comprising: a cap having an open end, a closed end, and an inwardly-projecting annular ridge; and a body having an open end, a closed end, and an outer surface having an annular groove, wherein the closed end of the body is adapted to slide inside the open end of the cap such that the inwardly-projecting annular ridge of the cap is engagable with the annular groove of the body.

The illustrative aspects of the present invention are designed to solve the problems herein described and other problems not discussed, which are discoverable by a skilled artisan.

BRIEF DESCRIPTION OF THE DRAWINGS

These and other features of this invention will be more readily understood from the following detailed description of the various aspects of the invention taken in conjunction with the accompanying drawings that depict various embodiments of the invention, in which:

FIG. 1 is a side-view of separate components of a multi-compartmented container according to a first embodiment of the invention;

It is noted that the drawings of the invention are not to scale. The drawings are intended to depict only typical aspects of the invention, and therefore should not be considered as limiting the scope of the invention. In the drawings, like numbering represents like elements between the drawings.

DETAILED DESCRIPTION

Figure 2A:
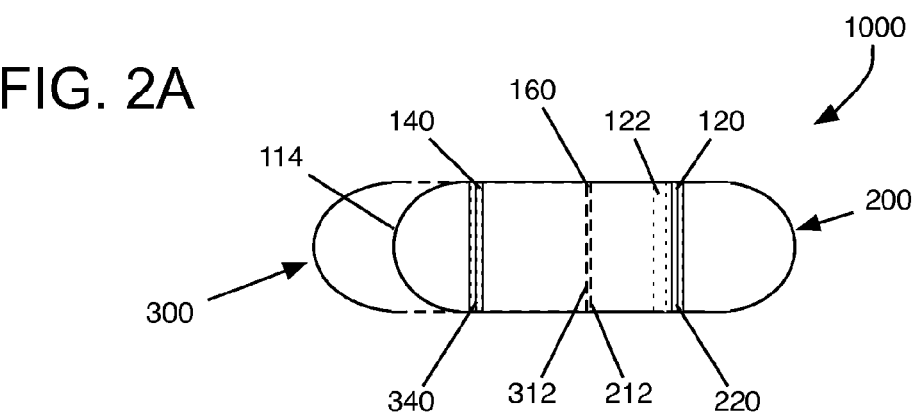
FIGS. 2A and 2B is a similar view to FIG. 1 with the components assembled, respectively in the pre-closed and closed positions.

As indicated above, the invention provides a multi-compartmented container and a dosage form suitable for the delivery of multiple doses of a compound and/or the delivery of more than one compound.

The term "multi-compartmented" means having more than one compartment, each compartment being distinct and separate from each other compartment.

The term "hard shelled" means having a shell that is deformable, but which returns to its undeformed shape upon the removal of a deforming force. Typically, such shells comprise less than about 25% water by weight, more preferably less than about 20% water by weight, and even more preferably about 14% water by weight.

Suitable compounds for delivery according to the invention include, but are not limited to, powder, liquid, and/or pellet forms of the following:

a) pharmaceuticals (also called pharmaceutical actives) such as betamethasone, thioctic acid, sotalol, salbutamol, norfenefrine, silymarin, dihydroergotamine, buflomedil, etofibrate, indomethacin, oxazepam, acetyldigitoxins, piroxicam, haloperidol, isosorbide mononitrate, amitriptyline, diclofenac, nifedipine, verapamil, pyritinol, nitrendipine, doxycycline, bromhexine, methylprednisolone, clonidine, fenofibrate, allopurinol, pirenzepine, levothyroxine, tamoxifen, metildigoxin, o-(B-hydroxyethyl)-rutoside, propicillin, aciclovirmononitrate, paracetamolol, naftidrofuryl, pentoxifylline, propafenone, acebutolol, 1-thyroxin, tramadol, bromocriptine, loperamide, ketofinen, fenoterol, ca-dobesilate, propranolol, minocycline, nicergoline, ambroxol, metoprolol, B-sitosterin, enalaprilhydrogenmaleate, bezafibrate, isosorbide dinitrate, gallopamil, xantinolnicotinate, digitoxin, flunitrazepam, bencyclane, depanthenol, pindolol, lorazepam, diltiazem, piracetam, phenoxymethylpenicillin, furosemide, bromazepam, flunarizine, erythromycin, metoclopramide, acemetacin, ranitidine, biperiden, metamizol, doxepin, dipotassiumchlorazepat, tetrazepam, estramustinephosphate, terbutaline, captopril, maprotiline, prazosin, atenolol, glibenclamid, cefaclor, etilefrin, cimetidine, theophylline, hydromorphone, ibuprofen, primidone, clobazam, oxaceprol, medroxyprogesterone, flecainide, Mg-pyridoxal-5-phosphateglutaminate, hymechromone, etofyllineclofibrate, vincamine, cinnarizine, diazepam, ketoprofen, flupentixol, molsidomine, glibornuride, dimethindene, melperone, soquinolol, dihydrocodeine, clomethiazole, clemastine, glisoxepid, kallidinogenase, oxyfedrine, baclofen, carboxymethylcystsin, thioredoxin, betahistine, 1-tryptophan, myrtol, bromelain, prenylamine, salazosulfapyridine, astemizole, sulpiride, benzerazid, dibenzepin, acetylsalicylic acid, miconazole, nystatin, ketoconazole, sodium picosulfate, colestyramate, gemfibrozil, rifampin, fluocortolone, mexiletine, amoxicillin, terfenadine, mucopolysaccharidpolysulfuric acid, triazolam, mianserin, tiaprofensaure, ameziniummethylsulfate, mefloquine, probucol, quinidine, carbamazepine, Mg-1-aspartate, penbutolol, piretanide, amitriptyline, caproteron, sodium valproinate, mebeverine, bisacodyl, 5-amino-salicyclic acid, dihydralazine, magaldrate, phenprocoumon, amantadine, naproxen, carteolol, famotidine, methyldopa, auranofine, estriol, nadolol, levomepromazine, doxorubicin, medofenoxat, azathioprine, flutamide, norfloxacin, fendiline, prajmaliumbitartrate, aescin acromycin, anipamil, benzocaine, β-carotene, cloramphenicol, chlorodiazepoxid, chlormadinoneacetate, chlorothiazide, cinnarizine, clonazepam, codeine, dexamethasone, dicumarol, digoxin, drotaverine, gramicidine, griseofulvin, hexobarbital hydrochlorothiazide, hydrocortisone, hydroflumethiazide, ketoprofen, lonetil, medazepam, mefruside, methandrostenolone, sulfaperine, nalidixic acid, nitrazepam, nitrofurantoin, estradiol, papaverine, phenacetin, phenobarbital, phenylbutazone, phenytoin, prednisone, reserpine, spironolactine, streptomycin, sulfamethizole, sulfamethazine, sulfamethoxazole, sulfamethoxydiazinon, sulfathiazole, sulfisoxazole, testosterone, tolazamide, tolbutamide, trimethoprim, tyrothricin, antacids, reflux suppressants, antiflatulents, antidopaminergics, proton pump inhibitors, H2-receptor antagonists, cytoprotectants, prostaglandin analogues, laxatives, antispasmodics, antidiarrhoeals, bile acid sequestrants, opioids, beta-receptor blockers, calcium channel blockers, diuretics, cardiac glycosides, antiarrhythmics, nitrates, antianginals, vasoconstrictors, vasodilators, ACE inhibitors, angiotensin receptor blockers, alpha blockers, anticoagulants, heparin, antiplatelet drugs, fibrinolytic, anti-hemophilic factor, haemostatic drugs, hypolipidaemic agents, statins, hypnotics, anaesthetics, antipsychotics, antidepressants (including tricyclic antidepressants, monoamine oxidase inhibitors, lithium salts, selective serotonin reuptake inhibitors), antiemetics, anticonvulsants, antiepileptics, anxiolytics, barbiturates, movement disorder drugs, stimulants (including amphetamines), benzodiazepine, cyclopyrrolone, dopamine antagonists, antihistamines, cholinergics, anticholinergics, emetics, cannabinoids, 5-HT antagonists, analgesics, muscle relaxants, antibiotics, sulfa drugs, aminoglycosides, fluoroquinolones, bronchodilators, NSAIDs, anti-allergy drugs, antitussives, mucolytics, decongestants, corticosteroids, beta-receptor antagonists, anticholinergics, steroids, androgens, antiandrogens, gonadotropin, corticosteroids, growth hormones, insulin, antidiabetic drugs (including sulfonylurea, biguanide/metformin, and thiazolidinedione), thyroid hormones, antithyroid drugs, calcitonin, diphosphonate, vasopressin analogs, contraceptives, follicle stimulating hormone, luteinising hormone, gonadotropin release inhibitor, progestogen, dopamine agonists, oestrogen, prostaglandin, gonadorelin, clomiphene, tamoxifen, diethylstilbestrol, antimalarials, anthelmintics, amoebicides, antivirals, antiprotozoals, vaccines, immunoglobulin, immunosuppressants, interferon, monoclonal antibodies, and mixtures thereof;

b) vitamins, e.g., fat-soluble vitamins such as vitamins A, D, E, and K, and water soluble vitamins such as vitamin C, biotin, folate, niacin, pantothenic acid, riboflavin, thiamin, vitamin B6, vitamin B12, and mixtures thereof;

c) minerals, such as calcium, chromium, copper, fluoride, iodine, iron, magnesium, manganese, molybdenum, phosphorus, potassium, selenium, sodium (including sodium chloride), zinc, and mixtures thereof;

d) dietary supplements such as herbs or other botanicals, amino acids, and substances such as enzymes, organ tissues, glandulars, and metabolites, as well as concentrates, metabolites, constituents, extracts of dietary ingredients, and mixtures thereof;

e) homoeopathic ingredients such as those listed in the Homeopathic Pharmacopoeia of the United States Revision Service (HPRS), and mixtures thereof. It must be recognized, of course, that the HPRS is periodically updated and that the present invention includes homeopathic ingredients that may be added to the HPRS; and mixtures in any combination of the foregoing.

It is also contemplated that mixtures of compatible ingredients can be included in one compartment and other ingredients which are not compatible with the contents of the first compartment or other ingredients which are desirably placed in a second compartment can also be used as part of the present invention. For example, a first compound may be included in one compartment in a powdered dosage form while a second compound may be included in a second compartment in a liquid dosage form. The ability to administer different dosage forms in a single dosage unit avoids not only any incompatibilities between the compounds and/or their dosage forms, but also the expense often incurred in reformulating one or the other compound into a compatible dosage form.

Referring now to the drawings, FIG. 1 shows an illustrative multi-compartmented container 1000 according to one embodiment of the invention, the container comprising a body 100, a cap 200 (also called "top cap"), and a capping member 300 (also called "bottom cap"). Each of the components constituted by the body 100, the cap 200 and the capping member 300 is formed by a hard-shell component preferably obtained by moulding. The body 100 and the cap 200 when assembled constitute a hard capsule. Each component is elongated along a longitudinal axis and has a substantially cylindrical shape over a section of its length. With respect to its longitudinal axis, each component includes an open end 112, 212, 312 and a closed end 114, 214, 314, respectively.

The components 100, 200, 300 are designed such that each of the cap 200 and the capping member 300 can be telescopically fitted onto the body 100 i.e can be coaxially and slideably mounted on the outer surface of the body.

The body 100 includes a pair of annular grooves 120, 122 near its open end 112 which a corresponding inwardly-projecting annular ridge 220 of top cap 200 may alternately engage. In a first position, annular ridge 220 engages first annular groove 120, forming a pre-lock position. The annular ridge 220 and the annular groove 120 constitute first complementary snap-fit members. As noted above, from a pre-lock position, top cap 200 may be removed from body 100 relatively easily (i.e. with a relatively low disengagement axial force) for filling on a filling machine.

Once filled, top cap 200 and body 100 are placed in a second position, wherein annular ridge 220 engages second annular groove 122. The annular ridge 220 and the annular groove 122 constitute second complementary snap-fit members. Said second snap-fit members are adapted to provide a retention force against axial disengagement of the cap from the body which is higher than the retention force provided by the first snap-fit members. In this position, top cap 200 and body 100 may be sealed with a sealing fluid, heat, or some other mechanism.

Unlike known capsules, as previously mentioned, container 1000 further includes a capping member 300, the open end 312 of which is adapted to coaxially slide over the closed end 114 of body 100, thereby forming a second volume or compartment between capping member 300 and body 100. This second volume may be filled with an additional dose of the compound contained between body 100 and top cap 200 (the first volume) or a dose of a different compound. Similar to the engagement of body 100 and top cap 200, body 100 includes a third annular groove 140 near its closed end 114 that may be engaged by an inwardly-projecting annular ridge 340 of capping member 300. The annular ridge 340 and the third annular groove 140 constitute complementary snap-fit means, whereby the capping member 300 is secured in a certain axial position on the capsule constituted by the body 100 and the cap 200, more precisely secured on the body 100. While not shown in the embodiment of FIG. 1, body 100 may optionally include an additional annular groove near its closed end, whereby body 100 and capping member 300 may alternately assume a pre-lock and locked position similar to that described above with respect to body 100 and top cap 200. In addition, while both the annular ridges and annular grooves in FIG. 1 are shown as continuous (i.e., unbroken in their path around a circumference of body 100, top cap 200, and capping member 300), annular ridges and grooves according to the invention may also be discontinuous.

Figure 2B:
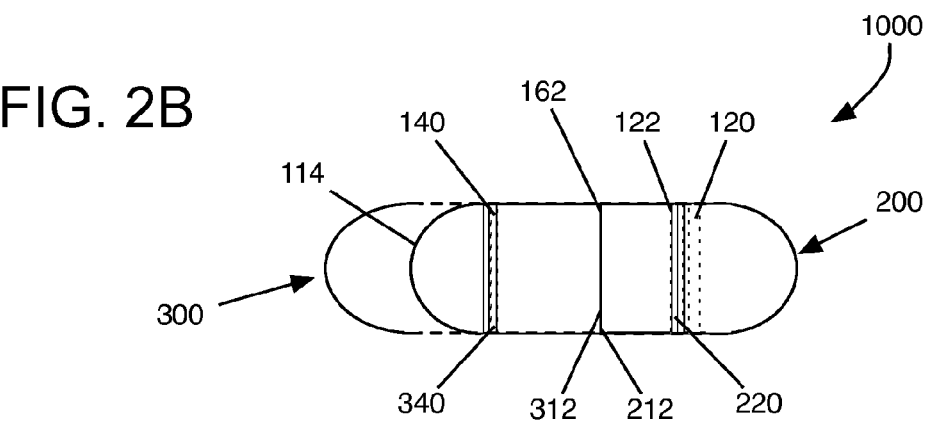

FIGS. 2A and 2B show the container 1000 of FIG. 1 in various positions and embodiments. In FIG. 2A, container 1000 is in its pre-lock position, wherein annular ridge 220 of top cap 200 is engaged with first annular groove 120 of body 100. Capping member 300 is fully inserted over the closed end 114 of body 100, such that annular ridge 340 of capping member 300 is engaged with third annular groove 140 of body 100. In the pre-lock position of FIG. 2A, a gap 160 exists between the open ends 212, 312 of top cap 200 and capping member 300.

In FIG. 2B, body 100 has been inserted further into top cap 200 such that annular ridge 220 has disengaged first annular groove 120 and engaged second annular groove 122 to assume a locked position. Gap 160 shown in FIG. 2A has been eliminated and the open ends 212, 312 of top cap 200 and capping member 300 have met to form a joint 162.

Figure 2C:
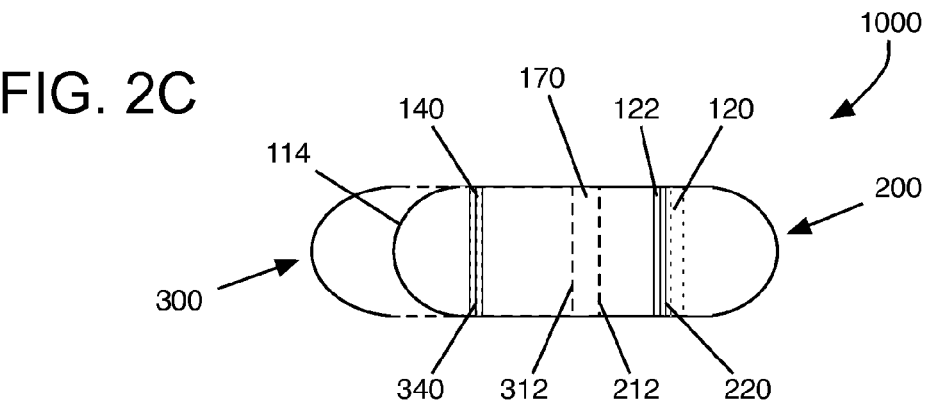
FIG. 2C is a similar view to FIG. 2B representing an alternative embodiment.

FIG. 2C shows an alternative embodiment, wherein a gap 170 remains between the open ends 212, 312 of top cap 200 and capping member 300 even after annular ridge 220 has been engaged with second annular groove 122. Such an embodiment may be useful, for example, where more rapid dissolution of container 1000, and particularly body 100, is desirable.

In some embodiments, body 100, top cap 200, and capping member 300 may be composed of different materials, combinations, or proportions of materials. For example, body 100 and top cap 200 may be composed of the same material having a first dissolution or disintegration rate and capping member 300 composed of a different material having a second dissolution or disintegration rate that is faster than the first dissolution or disintegration rate. As a result, the compound(s) contained between capping member 300 and body 100 will be released before the compound(s) contained between top cap 200 and body 100. This may be desirable where, for example, the efficacy of the compound(s) between top cap 200 and body 100 is enhanced by the presence of the compound(s) between capping member 300 and body 100. Such an embodiment may also be desirable where, for example, it is beneficial to deliver the same compound in multiple doses.

As noted above, commonly used materials for hard pharmaceutical capsules include gelatin (type A (derived from acid-treated raw materials) or type B (derived from alkali-treated raw materials)), hydroxypropylmethylcellulose (HPMC), and pullulan. Other materials may also be used, as will be recognized by one skilled in the art, including cellulose ethers, such as starches (e.g., waxy maize starch, tapioca dextrin, and derivatives thereof), carrageenan, and polymers or copolymers of (meth)acrylic acids and derivatives thereof.

Figure 3A:
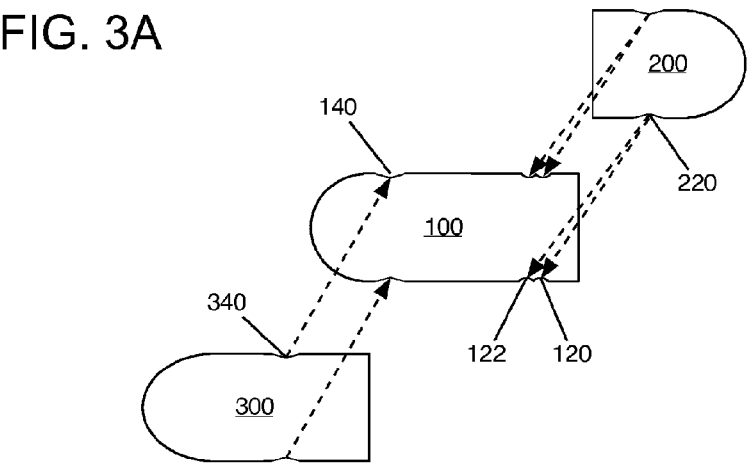
FIG. 3A illustrates the correspondence of the grooves and ridges of the components of a container as shown on FIG. 1.
Figure 3B:
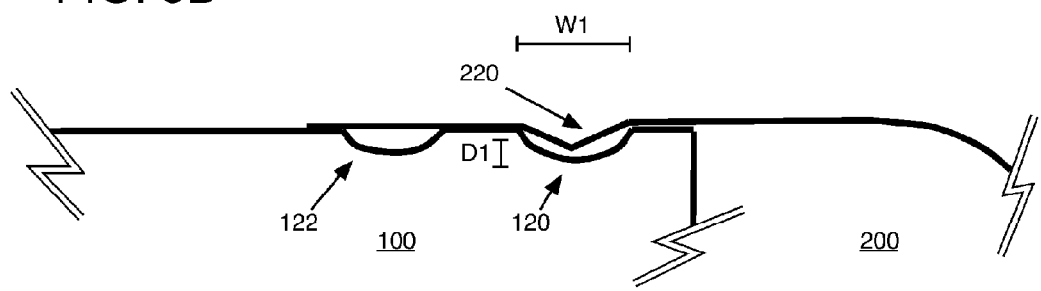
FIGS. 3B-F show enlarged schematic cross-sectional views of components of a multi-compartmented container according to a preferred embodiment of the invention.
Figure 3C:
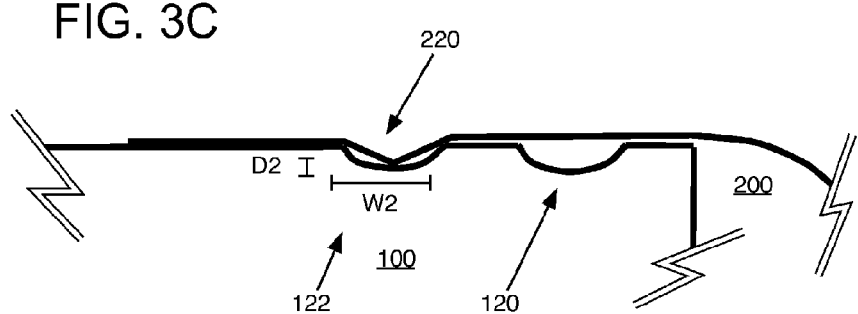

FIGS. 3A-C show more detailed views of the engagement of annular ridges 220, 340 and annular grooves 120, 122, 140. In FIG. 3A, it can be seen that annular ridge 340 of capping member 300 engages with third annular groove 140 of body 100 while annular ridge 220 of top cap 200 may be alternately engaged with first annular groove 120 and second annular groove 122 of body 100.

FIG. 3B shows a more detailed view of the "pre-lock" engagement of annular ridge 220 and first annular groove 120 according to one embodiment of the invention. As shown in FIG. 3B, first annular groove 120 has a first width W1 and first depth D1 such that annular ridge 220 does not extend to the full depth of first annular groove 120.

FIG. 3C shows the "lock" position following filling of container 1000. In FIG. 3C, annular ridge 220 has moved from first annular groove 120 to second annular groove 122, which has a second width W2 and second depth D2, each being less than first width W1 and first depth D1 of first annular groove 120. As shown in FIG. 3C, annular ridge 220 extends the full depth of second annular groove 122, providing an interference between body 100 and top cap 200 and a more secure engagement than when annular ridge 220 is engaged with first annular groove 120 The differences in depth and width of first annular groove 120 and second annular groove 122 make it possible to disengage top cap 200 from body 100 using different amounts of force. From the "pre-lock" position of FIG. 3B, top cap 200 and body 100 may be disengaged using less force than needed to disengage top cap 200 and body 100 from the "lock" position of FIG. 3C. This is advantageous when, as explained above, empty capsules are supplied to a filling machine in a "pre-lock" position of FIG. 3B, opened, filled, and closed to the "lock" position of FIG. 3C.

Figure 3D:
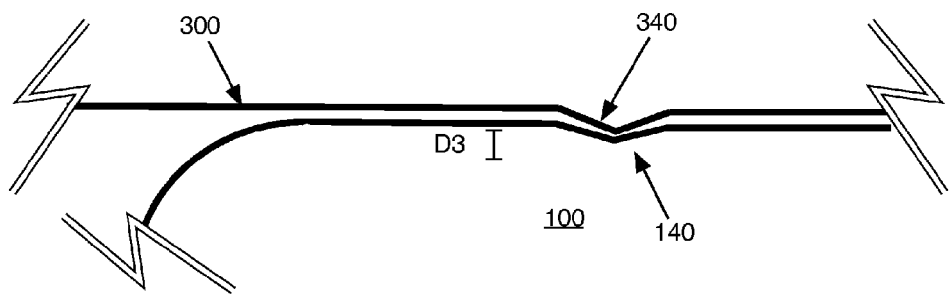

FIG. 3D shows a more detailed view of the engagement of annular ridge 340 of capping member 300 with third annular groove 140 having a depth D3 of body 100. In the embodiment shown in FIGS. 1-3A, body 100 includes only one annular groove near its closed end. As a result, capping member 300 and body 100 engage only in a "lock" position, such as that shown in FIG. 3D. In alternative embodiments, body 100 may include an additional annular groove near its closed end, such that capping member 300 and body 100 may engage in both "pre-lock" and "lock" positions, as with top cap 200 and body 100 described above.

Figure 3E:
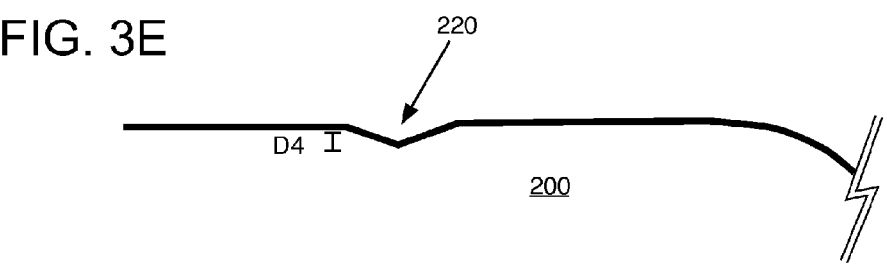
Figure 3F:
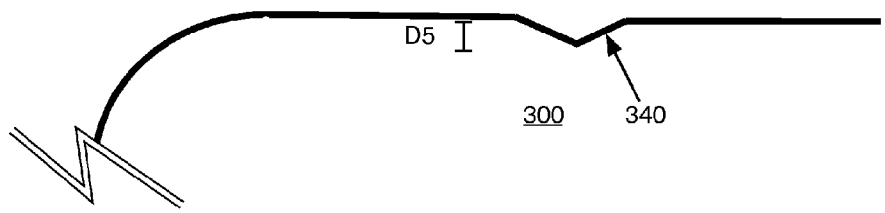

FIGS. 3E-F show more detailed views of the relative proportions of the annular ridges 220, 340 of top cap 200 and capping member 300. As can be seen, the depth D4 of annular ridge 220 is less than the depth D5 of annular ridge 340. The lesser depth of annular ridge 220 aids in disengaging top cap 220 and body 100 for the "pre-lock" position shown in FIG. 3B. If, as noted above, an additional annular groove is provided near the closed end of body 100 in order to permit engagement of capping member 300 in a "pre-lock" position, the depth D5 of annular ridge 340 may be similarly lessened.

Figure 4A:
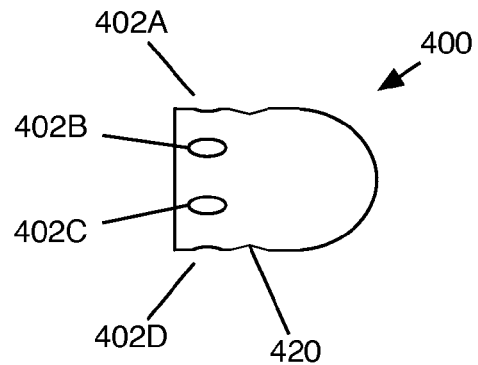
FIGS. 4A-B show schematic side and cross-sectional views, respectively, of a top cap according to an alternative embodiment of the invention.
Figure 4B:
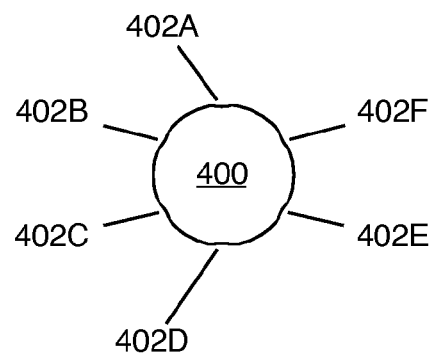

FIGS. 4A-B show side and cross-sectional views, respectively, of an alternative embodiment of top cap 400, wherein a plurality of inwardly-projecting columns 402A-F are provided. Top cap 400 is an alternative for top cap 200 in previous figures. Columns 402A-F increase friction between top cap 400 and body 100 (FIG. 1) as top cap 400 slides over body 100. Increased friction between top cap 400 and body 100 helps prevent accidental disengagement of top cap 400 and body 100.

Figure 5:
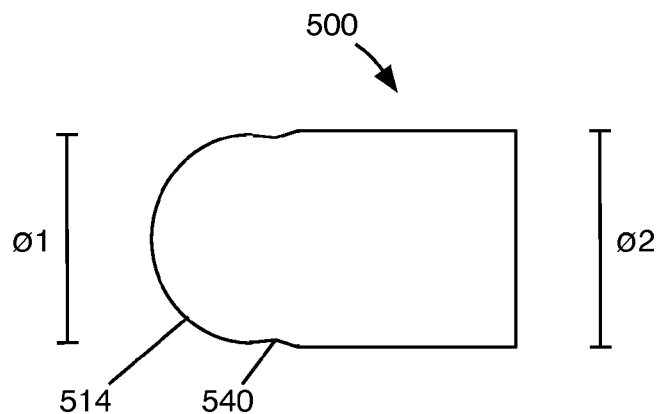
FIG. 5 shows a side view of a capping member according to an alternative embodiment of the invention.

FIG. 5 shows a side view of an alternative embodiment of capping member 500 having two diameters, ø1 and ø2, ø1 being smaller than ø2. Capping member 500 is an alternative for capping member 300 in previous figures. The smaller diameter of ø1 near the closed end 514 of capping member 500 provides additional friction between capping member 500 and body 100 (FIG. 1), particularly in the area of capping member 500 between its closed end 514 and annular ridge 540.

Table 1, below, shows dimensions of an illustrative container according to the invention. It should be noted that a wide range of dimensions are possible and within the scope of the invention, those shown in Table 1 being for purposes of illustration only. Larger, smaller, or other containers may have different absolute and/or relative dimensions.

TABLE 1

Illustrative Dimensions of Container Components

| Dimension (in mm) | Container (1000)* | Body (100) | Top Cap (200) | Capping member (300) |
|---|---|---|---|---|
| length | 23.5 | 16.7 | 9.7 | 12.471 |
| diameter | 6.95 | 6. | 6.85 | 6.85 (ø2) |
| gap (170) | 1.329 | NA | NA | NA |
| depth | NA | 0.008 (D3) | NA | NA |

*Numbers in parentheses correspond to elements shown in the figures.

A container having the dimensions shown in Table 1 results in a container having a maximum interference between the body 100 and top cap 200 of approximately 0.098 mm and a maximum interference between the body 100 and capping member 300 of approximately 0.077 mm. At their open ends 212, 312, top cap 200 and capping member 300 have interferences with body 100 of approximately 0.075 mm and approximately 0.034 mm, respectively.

Containers according to the invention may be manufactured, for example, using known dip coating methods and techniques. Such methods include dipping a pin, the outer surface of which is shaped as a container component (e.g., body, top cap, capping member) and includes the annular ridges and/or grooves described above, into a liquid composition, such as liquid HPMC, removing the pin from the liquid composition, and allowing the liquid composition to dry and/or cool, forming a hard shelled container component. Such components may then be removed from the pins and trimmed to a desired length according to known methods and techniques.

In one embodiment of the invention, one or more of the body (100, FIG. 1), top cap (200, FIG. 1), and capping member (300, FIG. 1) are tapered from their open ends (112, 212, 312, respectively, FIG. 1) to their closed ends (114, 214, 314, respectively, FIG. 1), such that a diameter at the open end is greater than a diameter at the closed end, with intermediate diameters gradually decreasing between the open end and the closed end. Such an embodiment facilitates removal of the dried component from its pin. Typically, such a taper has a range of between about 10 and about 15 microns per millimeter of component length, more preferably between about 11 and about 14 microns per millimeter, and even more preferably about 12 microns per millimeter.

In further embodiments of the invention (not shown), the container may include additional capping members telescopically and coaxially fitted one on the other or on the capsule, so as to define additional compartments between two successive capping members or between an additional capping member and the capsule. It will be appreciated that, in such embodiments, the container has more than two compartments.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of the invention as defined by the accompanying claims.

What is claimed is:

1. A container including:
   a hard shell capsule comprising a body and a cap telescopically fitted on the body in a common axial direction, said capsule defining a first compartment for accommodating a first dose of a compound, the cap having an open end and a closed end; and
   a capping member attached to the capsule and defining therebetween a second compartment for accommodating a second dose of a compound in a separate manner from the first dose, the capping member having an open end and a closed end;
   wherein the capping member is a hard shell telescopically and coaxially fitted on the capsule;
   wherein the body comprises a first annular groove and a second annular groove proximal to an open end of said body for alternating engagement with a corresponding annular ridge of the cap in a first position and second position respectively, the first position being a pre-lock position, and wherein the body further comprises a third annular groove proximal to a closed end of said body for engagement with an annular ridge of the capping member, wherein a distance between the first and second annular grooves is less than a distance between the second and third annular grooves;
   wherein, the open end of the capping member abuts the open end of the cap when the corresponding annular ridge of the cap is engaged with the second annular groove of the body and the annular ridge of the capping member is engaged with the third annular groove of the body.

2. A container according to claim 1, wherein the capping member and the capsule have complementary snap-fit means adapted to come into mutual engagement when the capping member is telescopically engaged on the capsule so as to secure the capping member on the capsule in a predetermined axial position.

3. A container according to claim 1, wherein the capping member is fitted on the body.

4. A container according to claim 2, wherein the capping member is fitted on the body and said complementary snap-fit means comprises the third annular groove formed on the body and the complementary annular ridge formed on the capping member.

5. A container according to claim 1, wherein the body and the cap have first complementary snap-fit members adapted to come into mutual engagement when the cap is telescopically engaged on the body so as to secure the cap on the body in the first position, the first position being a first predetermined axial position.

6. A container according to claim 5, wherein said first complementary snap-fit members comprise the first annular groove formed on the body and the complementary annular ridge formed on the cap.

7. A container according to claim 5, wherein the body and the cap have second complementary snap-fit members adapted to come into mutual engagement when the cap is telescopically further engaged on the body so as to secure the cap on the body in the second position, the second position being a second predetermined axial position, said second complementary snap-fit members being adapted to provide a retention force against axial disengagement of the cap from the body which is higher than the retention force provided by the first snap-fit members, said first axial position defining a pre-closed position and said second axial position defining a closed position.

8. A container according to claim 7, wherein said first complementary snap-fit members comprise the first annular groove formed on the body and the complementary annular ridge formed on the cap, said second complementary snap-fit members comprising said annular ridge formed on the cap and the second annular groove formed on the body, which is axially spaced from the first annular groove.

9. A container according to claim 1, wherein the capping member comprises a first capping member, the container further comprising at least one additional capping member, which comprises a hard shell telescopically and coaxially fitted either on the capsule or on the first capping member.

10. A dosage form comprising a container according to claim 1, further comprising a first dose of a first compound arranged in the first compartment and a second dose of a second compound arranged in the second compartment, wherein the first and second compounds are different.

11. A dosage form comprising a container according to claim 1, further comprising a first dose of a first compound in a first form arranged in the first compartment and a second dose of a second compound in a second form arranged in the second compartment, wherein the first and second forms are different.

* * * * *